(12) United States Patent
Enegren et al.

(10) Patent No.: US 7,018,336 B2
(45) Date of Patent: Mar. 28, 2006

(54) IMPLANTABLE SENSOR FLUSH SLEEVE

(75) Inventors: Bradley J. Enegren, Moorpark, CA (US); Marianne A. Kolopp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 85 days.

(21) Appl. No.: 10/034,740

(22) Filed: Dec. 27, 2001

(65) Prior Publication Data

US 2003/0125613 A1    Jul. 3, 2003

(51) Int. Cl.
*A61B 5/00* (2006.01)
(52) U.S. Cl. .................. 600/486; 600/345; 600/488; 600/505
(58) Field of Classification Search ........ 600/345–350, 600/486, 488, 505, 549; 606/15
See application file for complete search history.

(56) References Cited

U.S. PATENT DOCUMENTS

| | | | |
|---|---|---|---|
| 3,863,504 A * | 2/1975 | Borsanyi ..................... 73/706 |
| 4,210,029 A * | 7/1980 | Porter ......................... 73/705 |
| 4,432,366 A * | 2/1984 | Margules .................... 600/345 |
| 4,478,222 A * | 10/1984 | Koning et al. .............. 600/348 |
| 4,703,756 A * | 11/1987 | Gough et al. ............... 600/347 |
| 4,712,566 A * | 12/1987 | Hok ............................ 600/561 |
| 4,771,772 A | 9/1988 | DeWitt |
| 4,796,641 A * | 1/1989 | Mills et al. .................. 600/561 |
| 4,813,423 A * | 3/1989 | Miyasaka et al. ........... 600/311 |
| 4,936,310 A * | 6/1990 | Engstrom et al. ........... 600/486 |
| 5,166,990 A * | 11/1992 | Riccitelli et al. ............. 385/12 |
| 5,174,303 A | 12/1992 | Schroeppel |
| 5,322,609 A * | 6/1994 | Graham ................. 204/403.02 |
| 5,569,186 A | 10/1996 | Lord et al. |
| 5,830,209 A * | 11/1998 | Savage et al. ................ 606/15 |
| 5,891,094 A * | 4/1999 | Masterson et al. .......... 604/113 |
| 6,089,103 A * | 7/2000 | Smith ....................... 73/861.05 |
| 6,224,585 B1 * | 5/2001 | Pfeiffer ........................ 604/523 |
| 6,254,586 B1 | 7/2001 | Mann et al. |
| 6,358,244 B1 * | 3/2002 | Newman et al. .............. 606/15 |
| 2002/0007190 A1 * | 1/2002 | Wulfman et al. ........... 606/167 |
| 2003/0120255 A1 * | 6/2003 | Odell et al. ................. 604/500 |

\* cited by examiner

*Primary Examiner*—Robert L. Nasser
(74) *Attorney, Agent, or Firm*—Medtronic MiniMed, Inc.

(57) ABSTRACT

A apparatus and method for cleaning a sensor tip of an implantable sensor includes a flush sleeve directed towards the sensor tip, a fluid conduit in fluid communication with the flush sleeve, where fluid injected into a first end of a flush sleeve surrounding the sensor sprays off the sensor tip through at least one orifice located at the second end of the flush sleeve. The first end of the flush sleeve contains a fluid conduit and a septum, where a needle is used to pierce the septum to inject the fluid into the fluid conduit.

13 Claims, 2 Drawing Sheets ns. More specifically, the present invention relates to an implantable glucose sensor with cleaning features.

IMPLANTABLE SENSOR FLUSH SLEEVE

BACKGROUND OF THE INVENTION

1. Field of the Invention

The present invention relates generally to implantable sensors. More specifically, the present invention relates to an implantable glucose sensor with cleaning features.

2. Discussion of the Related Art

Recently, implantable glucose sensors for monitoring glucose concentration level in a patient fluid, such as blood, have been developed. These implantable or in vivo glucose sensors are designed to provide instantaneous reading of patient glucose concentration, where the tip of the glucose sensor is placed within a major blood vessel. Examples of some glucose sensors include U.S. Pat Nos. 4,650,547, 4,671,288, 4,781,798, 4,703,756, and 4,890,620. These implantable glucose sensors can be used in conjunction with an infusion pump system to deliver selected medication, such as insulin, to a patient in a scheduled or preprogrammed manner, including implantable infusion pumps to deliver insulin to the patient in discrete doses over an extended period of time.

However, a potential problem with implantable glucose sensors is that they can have a relatively short life span, often in the order of a few months. This stems from the fact that the implantable glucose sensors are located in a highly volatile environment, such as a large artery, and the human body tends to attack any foreign object placed in the body. Thus, clotting agents in the blood tend to cover and diminish the effectiveness of the sensor with the passage of time. In addition, the sensor can also be covered by proteins, fats, or other substances while the sensor is contact with human blood reducing the life of the sensors.

SUMMARY OF THE INVENTION

Accordingly, embodiments of the present invention are directed to a sensor apparatus and method with the added capability of a cleaning feature that substantially obviates one or more problems due to limitations and disadvantages of the related art.

Embodiments are directed to an implantable sensor apparatus for taking readings from a patient in vivo. The implantable sensor apparatus includes an implantable sensor, a flush sleeve, and a fluid conduit. The implantable sensor has a distal end with a sensor tip for direct contact with patient fluids. The flush sleeve is directed towards the sensor tip, and fluid received in the fluid conduit is used to spray the sensor tip, where the fluid conduit is in fluid communication with the flush sleeve. In additional embodiments, the implantable sensor also contains a connector fitting for supporting the implantable sensor within the patient.

In further embodiments, the fluid conduit contains a septum, where a needle is used to pierce the septum to inject the fluid into the fluid conduit. In still further embodiments, the flush sleeve surrounds the implantable sensor in a tight fit connection, and the flush sleeve contains at least one one-way valve near the sensor tip.

Further embodiments are directed to a method of cleaning a sensor tip of an implantable sensor. The method includes the steps of injecting fluid into a first end of a flush sleeve surrounding the sensor and spraying the sensor tip with the injected fluid through at least one orifice located at the second end of the flush sleeve. In further embodiments, the first end of the flush sleeve contains a fluid conduit and a septum, and a needle is used to pierce the septum to inject the fluid into the fluid conduit.

It is to be understood that both the foregoing general description and the following detailed description of the present invention are exemplary and explanatory and are intended to provide further explanation of the invention as claimed.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Embodiments of the present invention are directed to implantable sensors that measure a characteristic of a patient's body. In preferred embodiments, the characteristic is the glucose level, and the implantable sensor is placed in an artery or a vein. Although embodiments of the present invention are primarily described in the context of glucose sensors used in the treatment of diabetes, the embodiments of the invention are applicable to a wide variety of patient treatment programs where a physiological characteristic is monitored. For example, embodiments of the invention can be used to determine the status and/or levels of a variety of characteristics including those associated with agents such as hormones, cholesterol, medication concentrations, pH, oxygen saturation, viral loads (e.g., HIV), or the like. Also embodiments of the present invention are not limited to implantation in an artery or vein, but can be implanted in and/or through subcutaneous, dermal, sub-dermal, inter-peritoneal or peritoneal tissue. Such sensors typically communicate a signal from the implantable sensor to either an internal or external monitor. The implantable sensor is primarily adapted for use with blood. However, still further embodiments of the implantable sensor may be used in other bodily fluids, such as interstitial fluid, spinal fluid, saliva, urine, tears, sweat, or the like.

Figure 1:
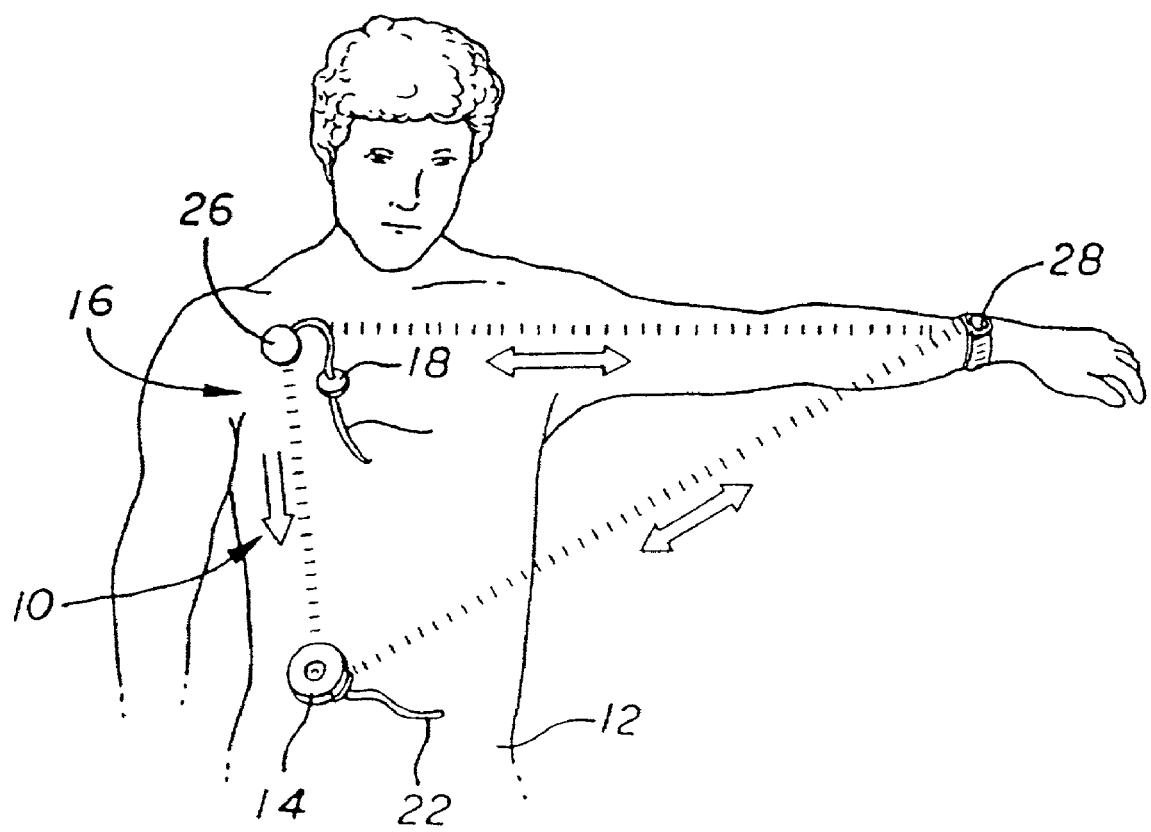
FIG. 1 is a schematic diagram illustrating a human environment in which preferred embodiments are implemented.

FIG. 1 is a schematic diagram illustrating a human environment in which preferred embodiments are implemented. As shown in FIG. 1, the preferred embodiments of the present invention are designed to be used with an infusion device system referred to generally in FIG. 1 by the reference numeral 10 to deliver selected medication to a patient 12. The system 10 generally includes an infusion device 14, which responds to control signals to deliver the fluids, such as, but not limited to, saline, drugs, vitamins, medication, proteins, peptides, insulin, neural transmitters, or the like, as needed to the patient. Embodiments of the present invention can utilize the infusion device 14 with an implantable sensor unit 16 in a closed-loop system. Alternatively, the implantable glucose sensor unit 16 may be used in an open loop system or alone to just monitor a condition of a patient.

In the preferred embodiments, the sensor unit 16 monitors patient glucose concentration level on a continuous, near-continuous or intermittent basis to provide appropriate control signals for the infusion device 14. Selected fluid, such as insulin for a diabetic patient, may then be administered to the patient in response to actual patient requirements as represented by a glucose measurement taken by the implantable sensor unit 16.

In accordance with an aspect of the invention, the sensor unit 16 includes a subcutaneously mounted connector fitting 18 for anchoring an in vivo glucose sensor 20 in a manner permitting convenient sensor removal and replacement. A connector fitting 18 provides a relatively simple and easily accessed structure for coupling the glucose sensor 20 with other system components, while permitting access to the glucose sensor 20 for removal and replacement. Although in the preferred embodiments, the infusion device 14 is also implanted within the patient 12 to form a closed-loop system, the sensor unit 16 can be used alternatively with external infusion device in a closed loop system and/or other open-loop systems. One example of a connector fitting 18 is disclosed in U.S. Pat. No. 5,569,186, entitled "Closed Loop Infusion Pump System With Removable Glucose Sensor," which is herein incorporated by reference. In alternative embodiments, other connection methods, such as, but not limited to, those utilized with pacemakers and/or pacemaker leads may be used.

In a preferred system arrangement, as viewed in FIG. 1, the infusion device 14 includes a small and substantially self-contained unit adapted for direct implantation into the body of the patient 12. The infusion device 14 includes a hermetically sealed infusion device housing constructed typically from a biocompatible material, such as, but not limited to, titanium or titanium alloy, and defining an internal fluid reservoir chamber for receiving and storing a supply of the selected fluid in liquid form, such as, but not limited to, insulin for a diabetic patient. In alternative embodiments, the infusion device housing may be formed out of other materials, such as, but not limited to, metal, ceramic, composites, glass, plastics, laminates, combinations, or the like, that are suitable for implantation in a patient. Embodiments of the infusion device housing may further encase a miniature dispensing pump and associated electronic control circuitry in combination with a battery power supply for operating the pump to deliver fluid doses to the patient via an appropriate catheter 22, or the like. In preferred embodiments, the control circuitry is suitably programmed and operated to deliver the fluid in accordance with individual patient need, including but not limited to providing insulin in a closed loop in response to glucose concentration measurement. In addition, preferred embodiments of the infusion device housing are designed to permit percutaneous refilling of the internal fluid reservoir without requiring surgical access to the implanted infusion device. For a more detailed description of the overall construction and operation of possible embodiments of implantable infusion devices of this general type, see U.S. Pat. Nos. 4,373,527 and 4,573,994, which are incorporated by reference herein.

As seen in FIG. 1, the sensor unit 16 is implanted within the patient 12 at a selected position for placement of the glucose sensor 20 in contact with a patient fluid, such as in intimate contact with patient blood within a cephalic vein. In alternative embodiments, other implantation sites, as discussed above, may be used. The connector fitting 18 is located at a convenient subcutaneous site for relatively easy palpable identification, and the sensor 20 extends from the connector fitting to a distal end positioned at a selected in vivo sensor position. In the preferred embodiments, a telemetry unit 26 (FIG. 1) is coupled to the connector fitting 18 through a cable 50 and functions to transmit glucose measurement signal information by means of radio telemetry. As viewed in FIG. 1, the telemetry unit 26 can transmit the glucose measurement information to the infusion device 14 for closed loop operation, or alternately to an externally located monitor 28. FIG. 1 illustrates the monitor 28 in the form of a wrist-worn device, although it will be understood that the monitor 28 may take other convenient forms, such as, but not limited to, an external infusion device. As is known in the art, the monitor 28 can be manipulated in response to information received and/or displayed to control infusion device operation through the use of radio telemetry signals. For instance, but not limited to, the monitor 28 may be programmed to automatically adjust infusion device operation according to glucose measurements, to recommend a treatment program to allow patient verification and manual initiation, or to simply display the glucose readings and permit manual entry of reprogramming commands.

Alternatively, instead of a telemetry unit 26, the cable 50 can connected directly to the control unit or circuit disposed internally within the implanted infusion device 14. With this system, radio telemetry transfer of glucose measurement information to the infusion device 14 is unnecessary. Instead, the information is transmitted directly through the use of the cable 50. Once again, the external monitor 28 may be used to read out or reprogram the infusion device 14 as previously described.

As shown in FIG. 1, the connector fitting 18 provides a convenient and relatively simple structure for anchoring the proximal end of the sensor 20 in electrical coupled relation with the telemetry unit 26. More particularly, the connector fitting 18 is mounted at the proximal end of the sensor 20 through a plug-in connector 40. In the preferred embodiments, the plug-in connector 40 is similar to a jack/plug combination, but alternatively, the plug-in connector 40 can be a Luer lock constructed at the proximal end of the sensor 20. In this position, the proximal end of the sensor 20 is seated and retained within the connector fitting 18. Embodiments of the connector fitting 18 may also include radially enlarged flanges 38 (or butterfly wings 38) having suture ports 42 formed to facilitate anchored connection of the fitting by sutures, or the like, to the subcutaneous muscle facia. Thus, the butterfly wings 38 help assure that sensor 20 will stay in the appropriate location.

Figure 2:
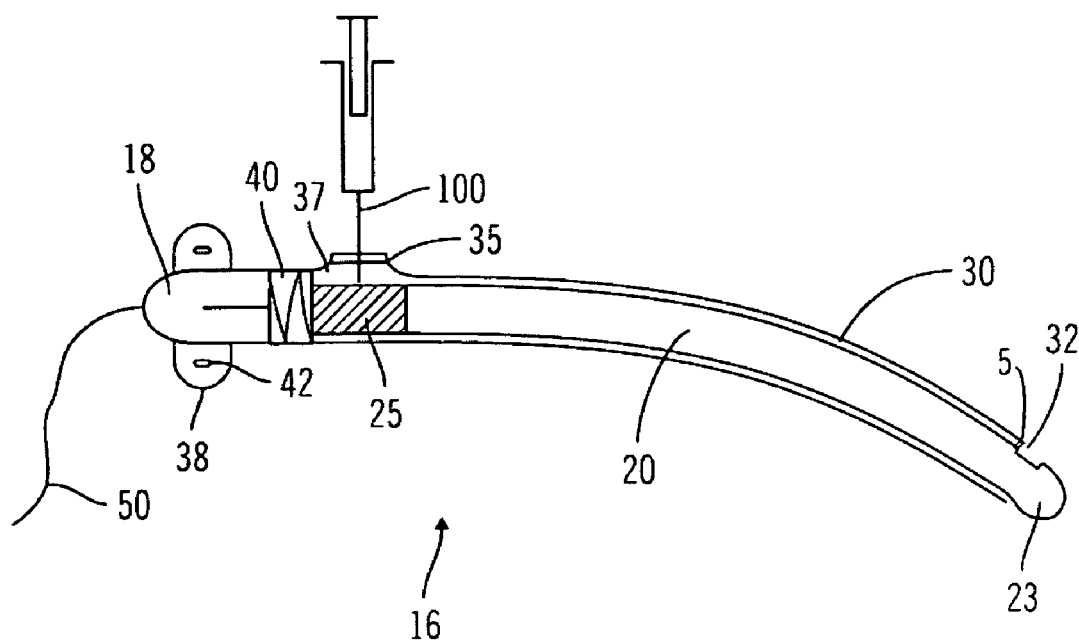
FIG. 2 is a cross-sectional view of the glucose sensor in accordance with the preferred embodiments of the present invention.

FIG. 2 is a cross-sectional view of the glucose sensor 20 in accordance with the preferred embodiments of the present invention. The glucose sensor 20 generally includes, in one preferred form, an improved implantable enzyme electrode of the general type described in U.S. Pat. Nos. 4,650,547; 4,671,288; 4,781,798; 4,703,756; and 4,890,620, which are incorporated by reference herein. Such enzyme electrodes include an elongated sensor 20 having a distal end defining a sensor tip 23 for direct contact with patient fluids, such as blood. The sensor tip 23 defines a conductivity sensor for measuring fluid conductivity changes in response to an enzymatic reaction typically involving the use of glucose oxidase to catalyze glucose in the presence of oxygen ($O_2$). Conductivity signals are transmitted through the sensor 20 via conductors to a proximal end of the sensor 20.

In alternative embodiments, different sensors technology may be used, such as, but not limited to an optical sensor. Preferably, an the implantable optical sensor would include a photo-reactive substance or compound that optically changes, fluoresces, or the like, or other suitable compounds that detect changing properties in the presence of a bodily fluid analyte, such as glucose or the like. The compounds can also be used to detect the level of an analyte that has been ingested, injected or placed inside the body, such as marker substances, or the like. For example, possible compounds, including but not limited to, produce a fluorescent change in the presence of a bodily fluid analyte are disclosed in U.S. Pat. No. 5,503,770 issued Apr. 2, 1996 to James et al. and entitled "Fluorescent Compound Suitable For Use In The Detection Of Saccharides"; U.S. Pat. No. 5,512,246 issued Apr. 30, 1996 to Russell et al. and entitled "Method and Means for Detecting Polyhydroxyl Compounds"; U.S. Provisional Application Ser. No. 60/007,515 to Van Antwerp et al. and entitled "Minimally Invasive Chemically Amplified Optical Glucose Sensor"; and U.S. Pat. No. 6,011,984 to Van Antwerp et al. and entitled "Detection of Biological Molecules Using Chemical Amplification", all of which are herein incorporated by reference. Other compounds using Donor Acceptor fluorescent techniques may be used, such as disclosed in U.S. Pat. No. 5,628,310 issued May 13, 1997 to Rao et al. and entitled "Method and Apparatus to Perform Trans-cutaneous Analyte Monitoring"; U.S. Pat. No. 5,342,789 issued Aug. 30, 1994 to Chick et al. and entitled "Method and Device for Detecting and Quantifying Glucose in body Fluids"; and U.S. Pat. No. 5,246,867 issued Sep. 21, 1993 to Lakowicz et al. and entitled "Determination and Quantification of Saccharides by Luminescent Lifetimes and Energy Transfer", all of which are herein incorporated by reference.

As shown in FIG. 2, in accordance with the preferred embodiments, the implantable sensor 20 includes a flush sleeve 30 in a tight fit connection surrounding the sensor 20, which allows fluid communication along the length of the sensor 20. Around the sensor tip 23, the flush sleeve 30 contains a small orifice 32, which comprises a one-way valve 5, to allow fluid to spray off the sensor tip 23. More than one orifice 32 can be placed at the distal end of the flush sleeve 30 to direct fluid to different locations of the sensor tip 23. Alternatively, the flush sleeve may be an elastomic cover, such as, but not limited to, rubber, plastic, silicone, polyurethane, polystyrene, or the like, that fits tightly around the sensor 20. When fluid is introduced into the flush sleeve, the flush sleeve expands under pressure so that the surrounding edge of the flush sleeve near the sensor tip separates from the sensor 20 to form at least one orifice 32 to permit the fluid to spray over the sensor tip. The edge of the sleeve may be configured and/or tailored to provide specific spray patterns, multiple orifices, selective openings, or the like, with the configuration being dependent on the type of environment where the sensor is implanted, the type of deposits to be removed, and the type of sensor.

In preferred embodiments, the flush sleeve 30 is in fluid communication with a fluid conduit 37 formed at the proximal end of the sensor 20. Fluid can be introduced into the fluid conduit 37 by means of a non-coring "huber" style needle 100, where the needle 100 introduces fluid through a septum 35. The septum 35 provides the needle 100 access to the fluid conduit 37, while providing a seal to substantially inhibit the incursion of external contaminants, such as bacteria, debris, or the like. This reduces the likelihood of developing an infection through contact with the external environment. In further embodiments, the septum 35 and fluid conduit 37 may include an anti-bacterial agent on the interior surface of the septum 35, or actually formed as an integral part of the septum 35 and conduit 37 material, to further minimize the chance of an infection. The combination of the septum 35 and the fluid conduit 37 acts as a syringe port, guiding the needle 100 to the flush sleeve 30. In the fluid conduit 37, the sensor 20 is surrounded by protector sleeve 25, which protects the sensor 25 and acts as a backstop to the needle 100. In preferred embodiments, the protector sleeve is made from titanium, although other material can be used to manufacture the protector sleeve. In alternative embodiments, other types of needles may be used, and the septum may be replaced or augmented with an input valve. In still other embodiments, the fluid conduit is eliminated and formed as an integral part of the flush sleeve.

In addition, certain embodiments may taper the ends of the flush sleeve 30 to improve the spraying process. The tapered ends would increase the pressure of the fluid out of the one or more orifices 32, and better direct the ejected fluid towards the surface of the sensor tip 23.

In use, fluid is injected into the fluid conduit 37 through the septum 35 using the needle 100. The fluid travels through the flush sleeve 30 and ejected out of the orifice 32. The fluid is used to clean the surface of the sensor tip 23 by knocking off any buildup of clots, encapsulation tissue, biological deposits, other debris, or the like, from the sensor tip 23. By cleaning the surface of the sensor tip 23, the readings by the sensor 20 can be restored, more accurate, and the life of the sensor 20 may be extended. In preferred embodiments, the fluid is a saline solution, but alternatively, the fluid can contain an anti-coagulant. A fluid that contains an anti-coagulant may assist in dissolving off the clots and/or biological deposits as well as spraying off the sensor tip 23.

In another use, the sensor 20 may change position over time, such that the sensor tip 23 is no longer in an optimal position. In this case, the injection of the fluid into the flush sleeve can also be used to reposition the sensor tip 23, as the fluid is injected from the orifice 32, by thrusting the sensor tip 23 away from the non-optimal position.

In preferred embodiments, the sensor 20, flush sleeve 30 and the connector fitting 18 are formed from a suitable medical-grade plastic, metal, glass, composites or the combination thereof that is bio-compatible. However, in alternative embodiments, the sensor 20, flush sleeve, and the connector fitting 18 are formed out of other suitable materials.

Additional Implementation Details

This concludes the description of the preferred embodiments of the invention. The following describes some alternative embodiments for accomplishing the present invention. The preferred embodiments were described in terms of flush sleeve 30 defining a flush channel around the sensor 20. In alternative embodiments, a separate catheter can be used to direct fluid at the sensor tip to remove the biological deposits. In addition, although preferred embodiments described an enzyme oxidase sensor to detect glucose levels, the sensor may be a different type of sensor using different technology and/or detecting other biological readings. Moreover, although the preferred embodiments described the infusion device, connector fitting, and sensor as separate components, the connector fitting may be provided as part of an integrated unit including the infusion device, where the sensor is disconnectable from the pump for removal and replacement, if desired.

Thus, the foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a description of the manufacture and use of the composition of the invention. Since many embodiments of the invention can be made without departing from the spirit and scope of the invention, the invention resides in the claims hereinafter appended.

What is claimed is:

1. An implantable sensor system for taking readings from a patient in vivo, the sensor system comprising:
   an implantable sensor having a distal end with a sensor tip for direct contact with patient fluids and a proximal end to anchor the implantable sensor within the patient;
   a flush sleeve directed towards the sensor tip;
   a rinsing fluid; and
   a fluid conduit in fluid communication with the flush sleeve,
   wherein the rinsing fluid received in the fluid conduit is used to spray the sensor tip,
   wherein the flush sleeve concentrically surrounds the implantable sensor around a substantially common axis, such that the sensor is within the flush sleeve,
   wherein the fluid conduit contains a septum and a protector sleeve, wherein the septum is pierced by a needle injected into the patient to deliver the rinsing fluid into the fluid conduit, and wherein the protector sleeve acts as a backstop to prevent the needle from penetrating the sensor.

2. The sensor system of claim 1, further comprising a connector fitting for supporting the implantable sensor within the patient.

3. The sensor system of claim 2, wherein the sensor is plugged into the connector fitting, and the connector fitting is affixable internally to the patient.

4. The sensor system of claim 2, wherein the connector fitting is connected to a telemetry unit to transmit readings from the implantable sensor.

5. The sensor system of claim 1, wherein the flush sleeve surrounds the implantable sensor in a tight fit connection.

6. The sensor system of claim 5, wherein the flush sleeve contains at least one one-way valve near the sensor tip.

7. The sensor system of claim 1, wherein the fluid conduit is located at a proximal end of the sensor.

8. The sensor system of claim 7, wherein the proximal end of the sensor is covered by a protector sleeve.

9. The sensor system of claim 1, wherein the rinsing fluid is a saline solution.

10. The sensor system of claim 1, wherein the rinsing fluid contains an anti-coagulant.

11. An implantable multi-lumen sensor system for taking readings from a patient in vivo, the sensor system comprising:
    an inner lumen comprising an implantable sensor having a distal end with a sensor tip for direct contact with patient fluids and a proximal end to anchor the implantable sensor within the patient;
    an outer lumen comprising a flush sleeve surrounding the inner lumen in a substantially coaxial manner, such that the inner lumen is within the outer lumen; and
    a rinsing fluid received in the flush sleeve to spray the sensor tip,
    wherein the flush sleeve farther contains a septum and a protector sleeve, wherein the septum is pierced by a needle injected into the patient to deliver the rinsing fluid into the flush sleeve, and wherein the protector sleeve acts as a backstop to prevent the needle from penetrating the sensor.

12. The sensor system of claim 11, wherein the flush sleeve surrounds the inner lumen in a tight fit connection.

13. The sensor system of claim 12, wherein the flush sleeve contains at least one one-way valve near the sensor tip.

* * * * *